United States Patent
Etter et al.

(10) Patent No.: US 6,855,156 B2
(45) Date of Patent: Feb. 15, 2005

(54) OPHTHALMIC MICROSURGICAL INSTRUMENT

(75) Inventors: Heinz Etter, Winterthur (CH); Jürg Attinger, Stein am Rhein (CH); Werner Maag, Glarus (CH)

(73) Assignee: Grieshaber & Co. AG Schaffhausen, Schaffhausen (CH)

( * ) Notice: Subject to any disclaimer, the term of this patent is extended or adjusted under 35 U.S.C. 154(b) by 227 days.

(21) Appl. No.: 09/929,186

(22) Filed: Aug. 14, 2001

(65) Prior Publication Data

US 2001/0056286 A1 Dec. 27, 2001

(30) Foreign Application Priority Data

Oct. 19, 2000 (CH) ................................. 2000 2049/00
May 16, 2001 (CH) ................................. 2000 0908/01

(51) Int. Cl.[7] ............................................. A61B 17/28
(52) U.S. Cl. ...................................... 606/205; 606/208
(58) Field of Search ............................. 606/174, 210, 606/170, 205, 206, 157; 81/305, 304

(56) References Cited

U.S. PATENT DOCUMENTS 4,402,420 A * 9/1983 Chernack ................... 220/266
5,290,302 A * 3/1994 Pericic ....................... 606/167
5,308,357 A * 5/1994 Lichtman ................... 606/205
5,370,658 A * 12/1994 Scheller et al. ............. 606/205
5,868,761 A * 2/1999 Nicholas et al. ............ 606/143
5,893,873 A * 4/1999 Rader et al. ................ 606/205
6,024,748 A * 2/2000 Manzo et al. ............... 606/153

FOREIGN PATENT DOCUMENTS

DE            90 16 261 U        2/1991

* cited by examiner

Primary Examiner—Vy Bui
(74) Attorney, Agent, or Firm—Henry M. Feiereisen; Ursula B. Day

(57) ABSTRACT

A surgical instrument, includes an elongate housing having two housing parts. Disposed between the housing parts is a support arm having one axial end connected to the housing parts. A functional unit is secured to the other axial end of the support arm and includes a rod and an operating member acted upon by the rod, when the housing parts are squeezed together. A force-transmitting unit having an adjusting member is operatively connected to the rod, for translating a movement of the housing parts in a direction substantially transverse to the support arm, as the housing parts are squeezed together, into a linear axial movement of the adjusting member, to thereby actuate the operating member.

24 Claims, 6 Drawing Sheets

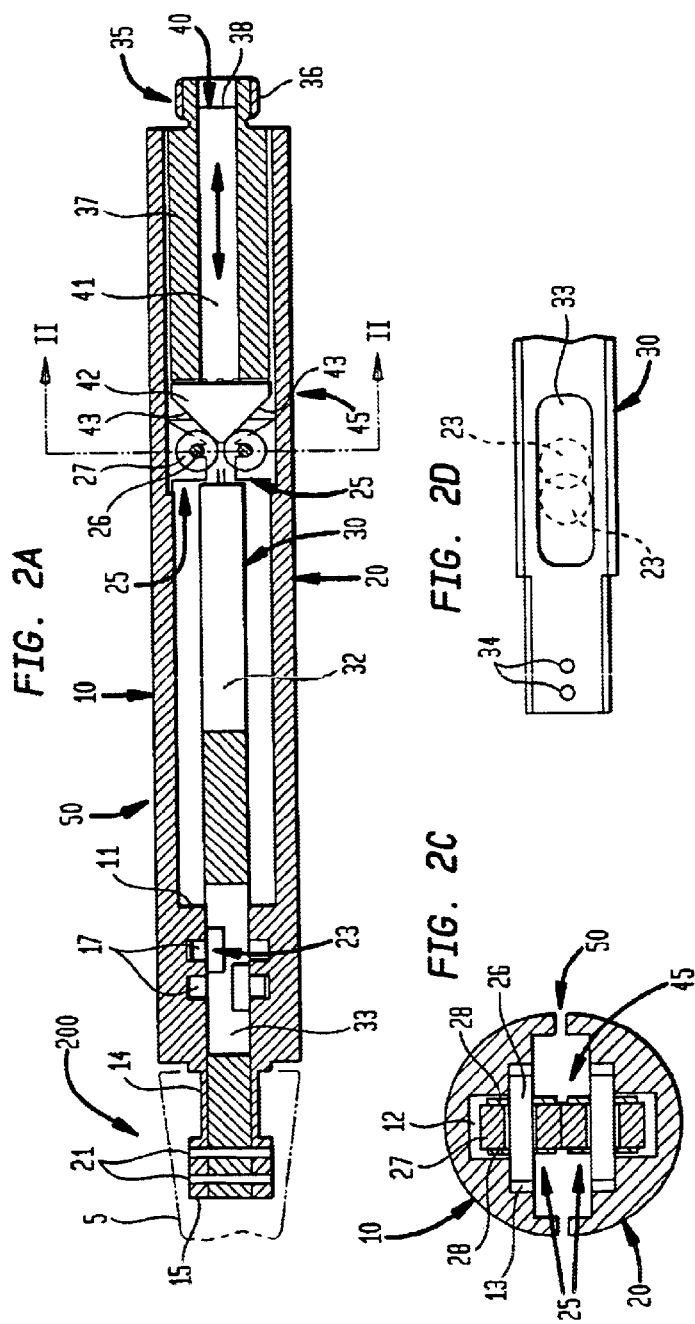

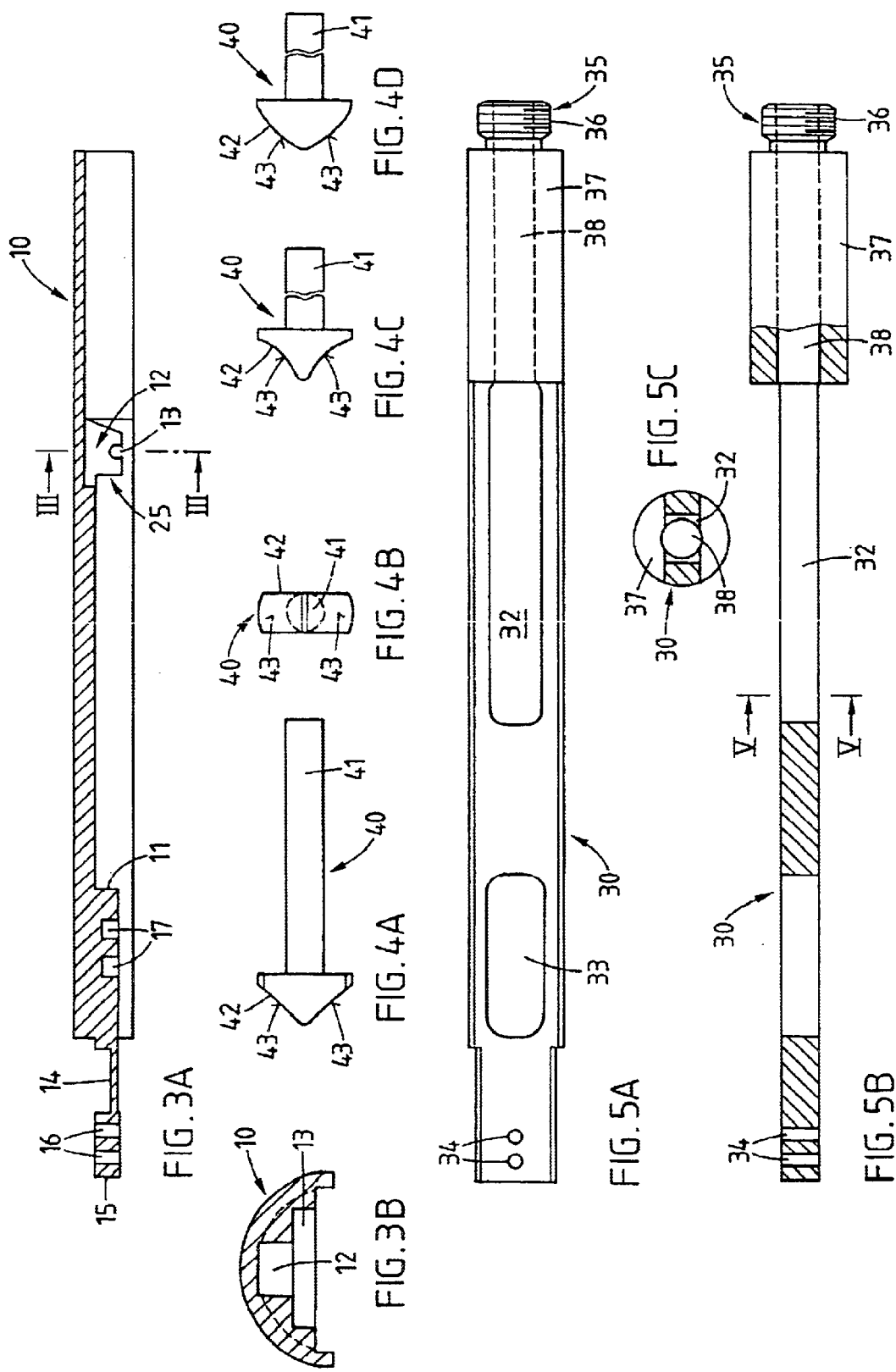

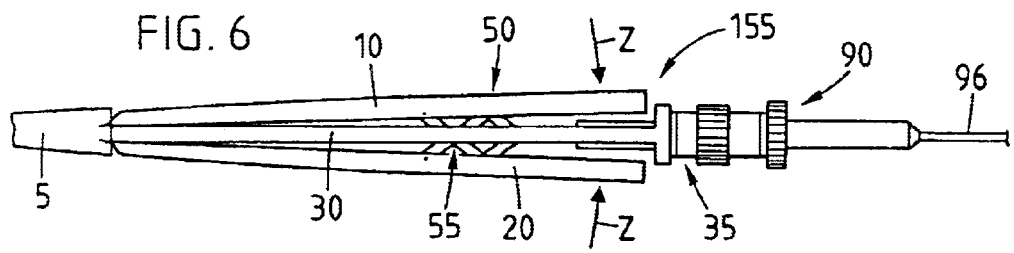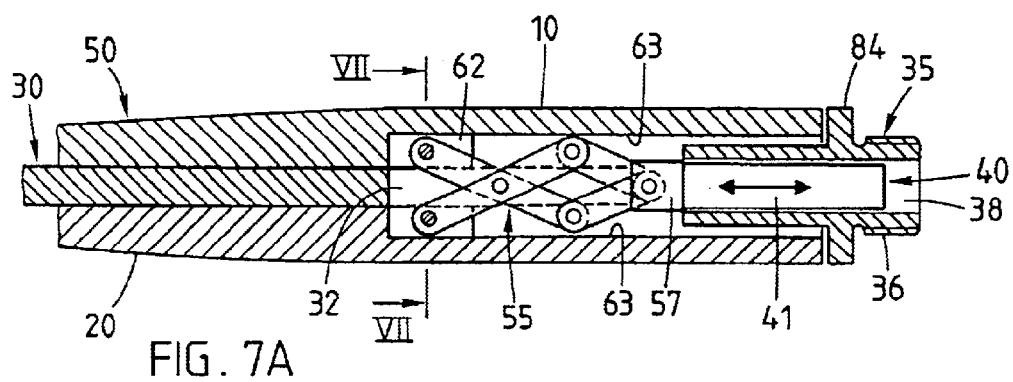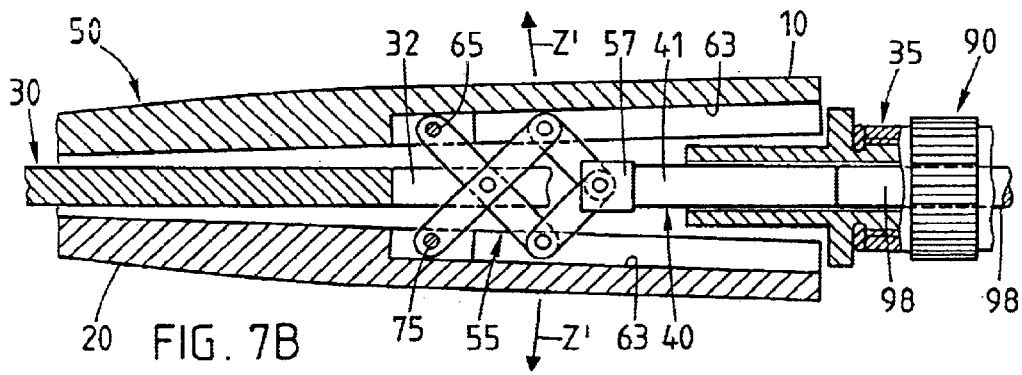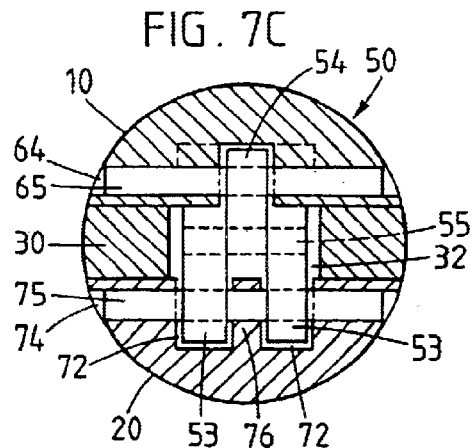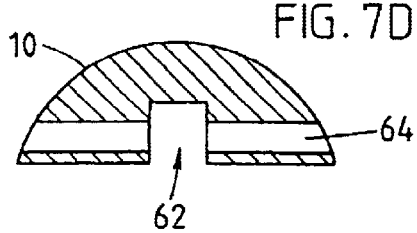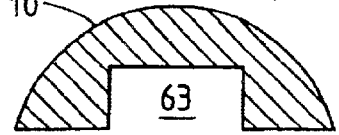

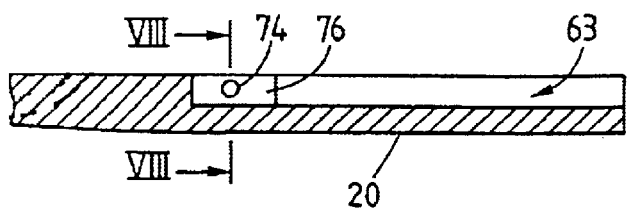
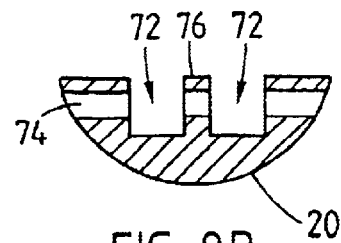
FIG. 8A FIG. 8B
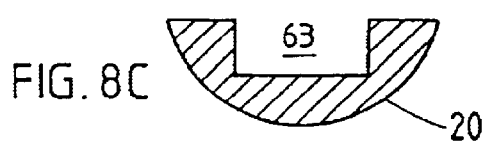
FIG. 8C
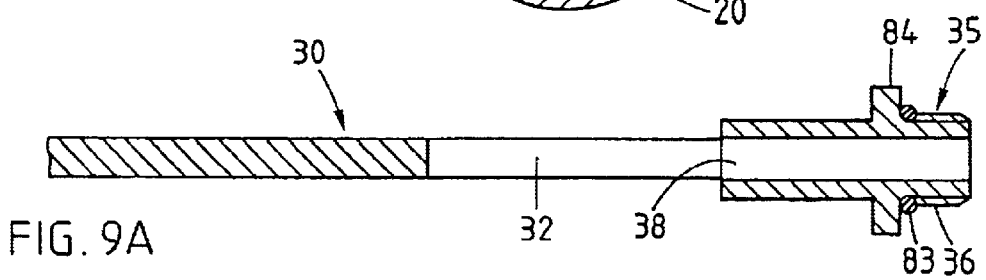
FIG. 9A
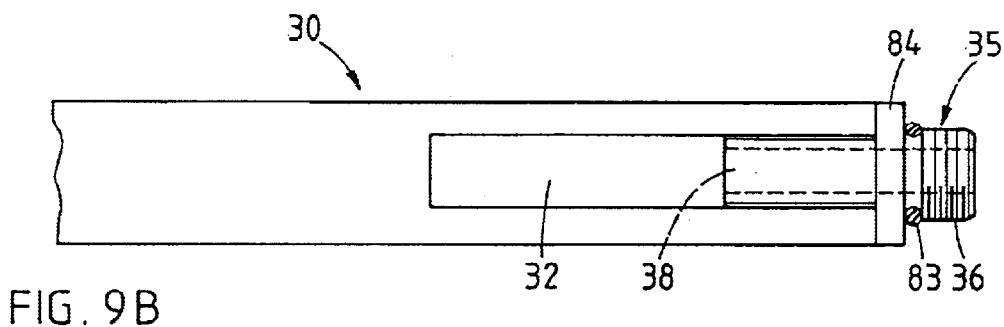
FIG. 9B
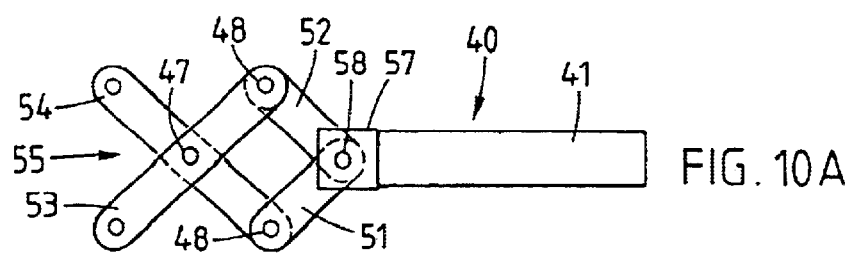
FIG. 10A
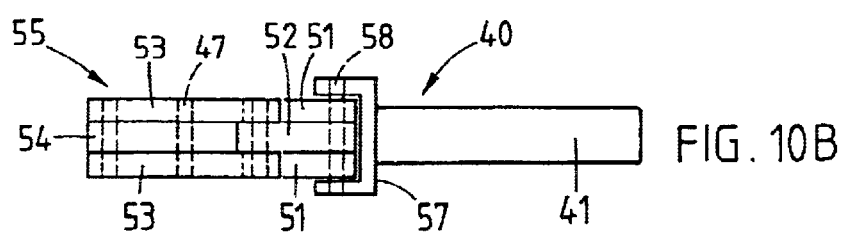
FIG. 10B

OPHTHALMIC MICROSURGICAL INSTRUMENT

CROSS-REFERENCES TO RELATED APPLICATIONS

This application claims the priorities of Swiss Patent Applications, Ser. No. 2000 2049/00, filed Oct. 19, 2000, and Ser. No. 2001 0908/01, filed May 16, 2001, the subject matter of which is incorporated herein by reference.

BACKGROUND OF THE INVENTION

The present invention relates to a surgical instrument, especially but not exclusively for carrying out ophthalmologic procedures.

U.S. Pat. No. 5,290,302 describes a surgical instrument having a housing which forms a generally cylindrical handpiece and is split longitudinally into two elongate housing parts of substantially semi-circular configuration. The housing parts are pivotally mounted at one end to a support member and acted upon at their other end by a spring element by which the housing parts are urged into a position away from one another. When squeezing the housing parts together, levers, disposed in a forward area of the support member, implement a rotation movement upon an elongate tube as well as upon a shaft coaxially retained in the tube to move jaws of a clamping element or cutting element to one another.

It would be desirable and advantageous to provide an improved surgical instrument which obviates prior art shortcomings.

SUMMARY OF THE INVENTION

According to one aspect of the present invention, a surgical instrument includes an elongate housing having two housing parts; a support arm disposed between the housing parts and having opposite axial ends, with one of the axial ends connected to a rear end of the housing parts; a functional unit configured for attachment to the other one of the axial ends of the support arm, thereby spreading the housing parts apart, wherein the functional unit includes a rod and an operating member acted upon by the rod, as the housing parts are squeezed together; and a force-transmitting unit having an adjusting member operatively connected to the rod, for translating a movement of the housing parts in a direction substantially transverse to the support arm, as the housing parts are squeezed together, into a linear axial movement of the adjusting member, to thereby actuate the operating member via the rod.

BRIEF DESCRIPTION OF THE DRAWING

Other features and advantages of the present invention will be more readily apparent upon reading the following description of a preferred exemplified embodiment of the invention with reference to the accompanying drawing, in which:

FIG. 2A is a sectional view, on an enlarged scale, of the surgical instrument of FIG. 1A in the operative position of the functional unit;

FIG. 2B is a sectional view, on an enlarged scale of the surgical instrument of FIG. 1A in the idle position of the functional unit;

FIG. 2C is a sectional view of the surgical instrument, taken along the line II—II in FIG. 2A;

FIG. 2D is a plan view of a partial section of the support arm of the surgical instrument for support of the functional unit with stop members located in a recess;

FIG. 3A is a sectional view of a housing part of the surgical instrument;

FIG. 3B is a sectional view of the surgical instrument, taken along the line III—III in FIG. 3A;

FIG. 4A is a side elevation of an adjusting member for use in the surgical instrument, shown in FIGS. 2A to 2C;

FIG. 4B is an end view of the adjusting member;

FIG. 4C is a side elevation of a variation of an adjusting member for use in the surgical instrument;

FIG. 4D is a side elevation of still another variation of an adjusting member for use in the surgical instrument;

FIG. 5A is a plan view of a support arm of the surgical instrument for support of the functional unit;

FIG. 5B is a partially sectional view of the support member;

FIG. 5C is a section of the support member, taken along the line V—V in FIG. 5B;

FIG. 6 is a side elevation of another embodiment of a surgical instrument according to the present invention in an idle position;

FIG. 7A is a fragmentary sectional view, on an enlarged scale, of the surgical instrument of FIG. 6 in an operative position;

FIG. 7B is a fragmentary sectional view, on an enlarged scale, of the surgical instrument of FIG. 7A in the idle position;

FIG. 7C is a sectional view of the surgical instrument, taken along the line VII—VII in FIG. 7A;

FIG. 7D is a sectional view of a housing part of the surgical instrument;

FIG. 7E is a sectional view of the housing part of FIG. 7D, illustrating the formation of a track;

FIG. 8A is a cutaway view of another housing part of the surgical instrument of FIG. 7A;

FIG. 8B is a sectional view of the housing part, taken along the line VIII—VIII in FIG. 8A;

FIG. 8C is a sectional view of the other housing part of FIG. 8A, illustrating the formation of a track;

FIG. 9A is a sectional view of the support arm of the surgical instrument of FIG. 6;

FIG. 9B is a plan view of the support arm of FIG. 9A;

FIG. 10A is a side elevation, on an enlarged scale, of a force-transmitting unit for the surgical instrument of FIG. 6A;

FIG. 10B is a plan view of the force-transmitting unit of FIG. 10A;

DETAILED DESCRIPTION OF PREFERRED EMBODIMENTS

Figure 1A:
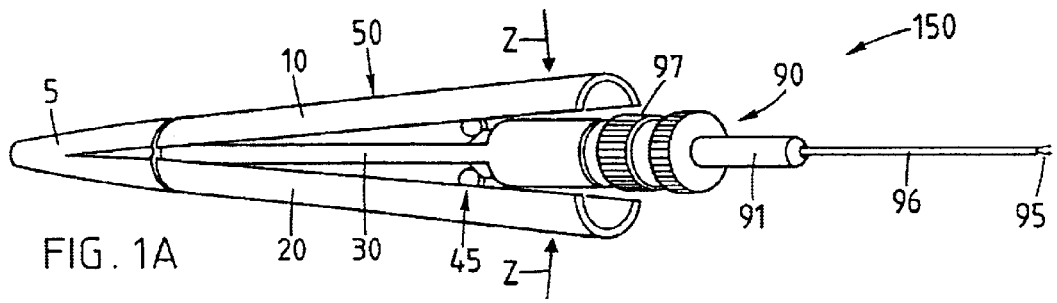
FIG. 1A is a schematic, perspective illustration, on an enlarged scale, of one embodiment of a surgical instrument according to the present invention with attached functional unit.

Throughout all the Figures, same or corresponding elements are generally indicated by same reference numerals.

Figure 1B:
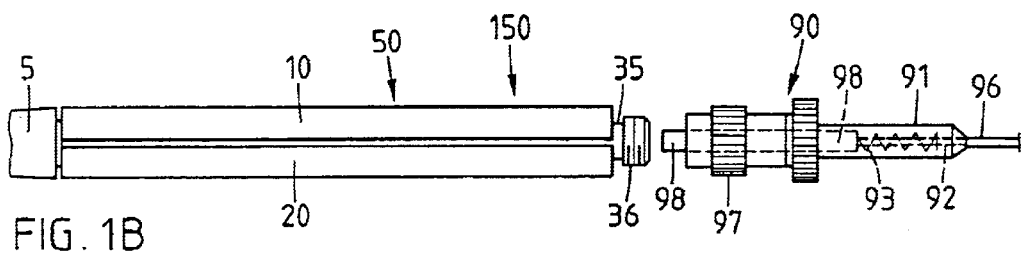
FIG. 1B is a schematic side elevation of the surgical instrument, with the functional unit being detached.

Turning now to the drawing, and in particular to FIG. 1A, there is shown a schematic, perspective illustration, on an enlarged scale, of one embodiment of a surgical instrument according to the present invention, generally designated by reference numeral 150, especially but not exclusively for use in surgical procedures on the eye. The surgical instrument 150 includes a housing 50forming a handpiece and comprised of two elongate housing parts 10, 20. Placed over the rear end 200 of the housing parts 10, 20 is an end cap 5. Disposed between the housing parts 10, 20 is a substantially flat elongate support arm 30 for attachment of a functional unit, generally designated by reference numeral 90. As shown in FIG. 1B, the support arm 30 has a head portion 35 which is configured for insertion of the functional unit 90 and has an outer thread 36 for threaded engagement of a coupling nut 97, when the functional unit 90 is mounted to the surgical instrument 150, so as to secure the functional unit 90 onto the surgical instrument 150. In this way, different types of functional units 90 can be quickly attached and detached from the surgical instrument 150.

Figure 1C:
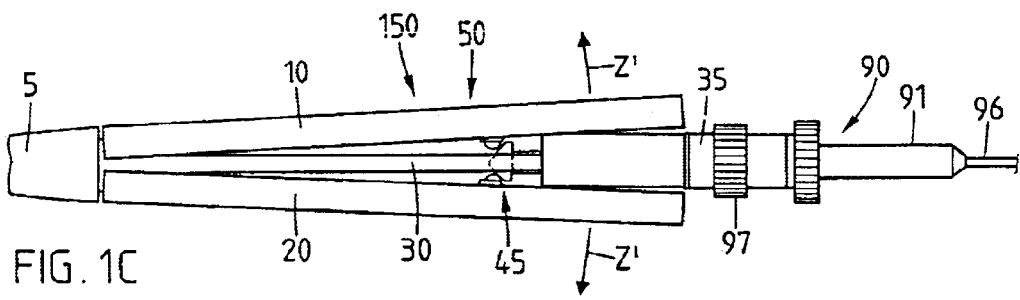
FIG. 1C is a schematic side elevation of the surgical instrument of FIG. 1A.

In the area of the end cap 5, the housing parts 10, 20 are pivotally mounted to the support arm 30 so as to be swingable about a pivot point in opposition to an inherent elastic spring force into an open position in which the housing parts 10, 20 are moved apart in the direction of arrow Z', when the functional unit 90 is attached to the head portion 35, as this is shown in FIGS. 1A and 1C. When the functional unit 90 is detached from the housing 50 of the surgical instrument 150, as shown in FIG. 1B, the housing parts 10, 20 assume a closed position as a consequence of their inherent elasticity.

Figure 1D:
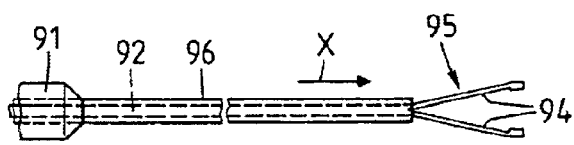
FIG. 1D is a schematic view of a clamp-type functional unit for use with the surgical instrument according to the present invention, with the functional unit being shown in an idle position of the surgical instrument.
Figure 1E:
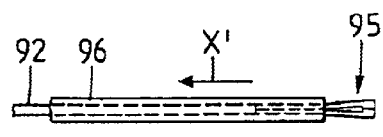
FIG. 1E is a schematic view of the clamp-type functional unit of FIG. 1D in the operative position and FIG. 1F is a schematic view of a cutter-type functional unit for use with the surgical instrument according to the present invention.
Figure 1F:
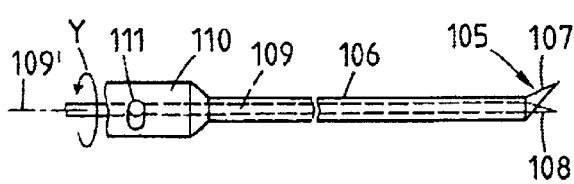
Figure 11A:
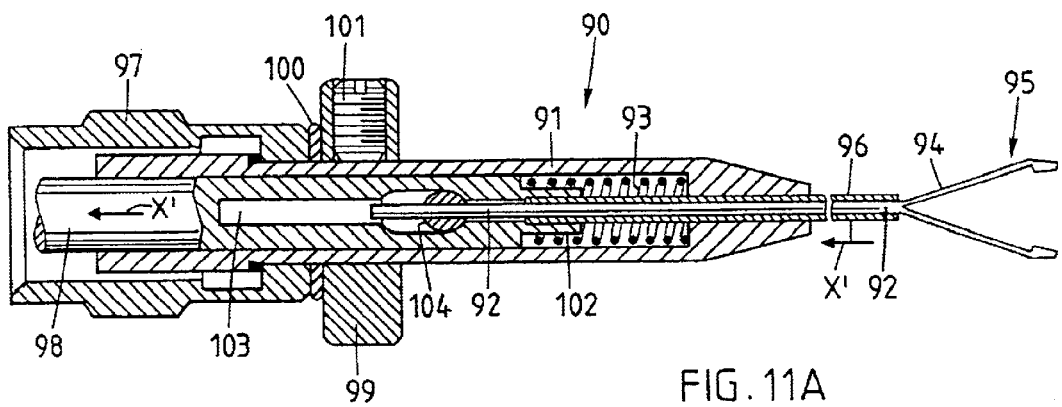
FIG. 11A is a sectional view of a clamp-type functional unit for use with the surgical instrument according to the present invention, with the functional unit being shown in an idle position of the surgical instrument.
Figure 11B:
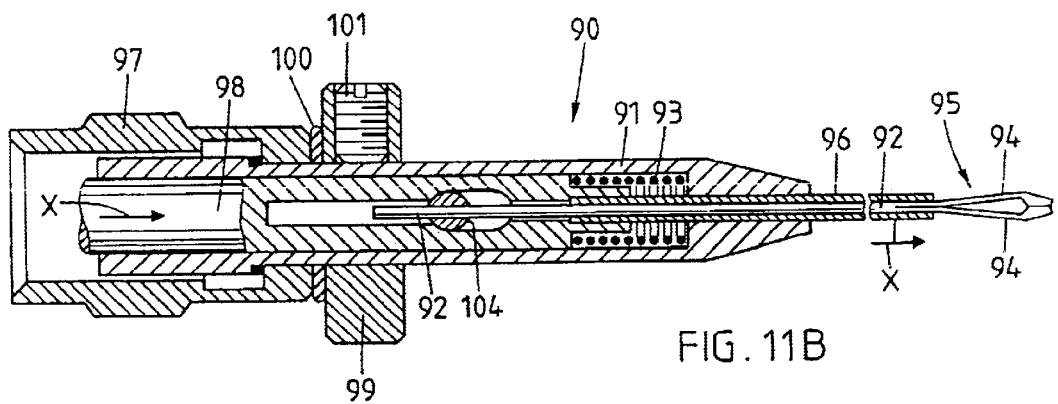
FIG. 11B is a sectional view of the clamp-type functional unit of FIG. 1D in the operative position.
Figure 11C:
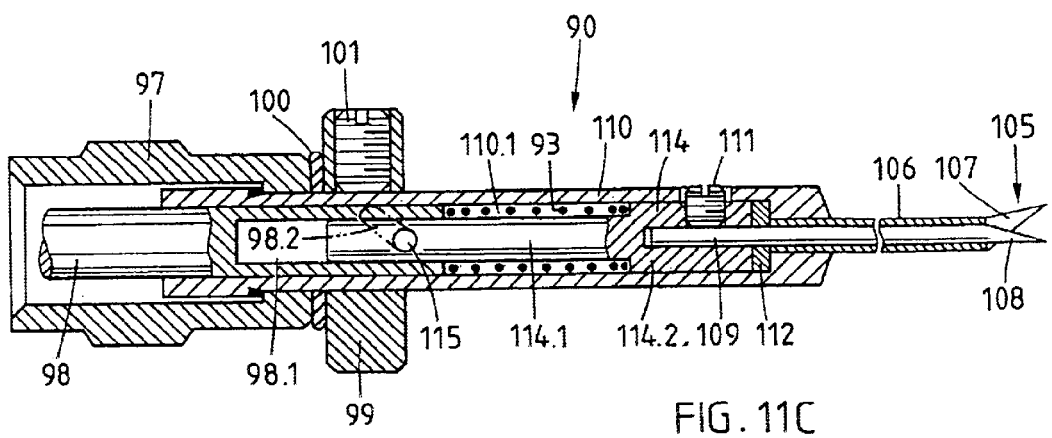
FIG. 11C is a sectional view of a cutter-type functional unit for use with the surgical instrument according to the present invention.

As shown in FIGS. 1D to 1F and in particular in FIGS. 11A to 11C, the functional unit 90 may be configured as a clamp-type operating member or as a cutter-type operating member. The clamp-type operating member shown in FIGS. 1D and 11A includes a guide sleeve 91 which is received in the coupling nut 97 and extends out through an opening of the coupling nut 97. A set ring 99 and interposed washer 100 are placed over the sleeve 91 and secured in place by a threaded pin 101 so that the sleeve 91 and the coupling nut 97 form a unitary structure. A rod 98 is movably received in the sleeve 91 and is formed with a coupling nut distal prolongation 102 for attachment of one end of a compression spring 93. The other end of the compression spring 93 bears against a confronting inside wall surface of the sleeve 91. The rod 98 issues from the rear of the sleeve 91 (FIG. 1B) for insertion into the head portion 35 and includes an inner blind bore 103 for receiving a tube 96 which projects from the front end of the sleeve 91 and is securely fixed at its rear end to the rod 98, e.g. by gluing or welding. Disposed in the tube 96 is a shaft 92 which is secured against axial displacement and fixed in place by a set screw 104. The shaft 92 juts out from the tube 96 and terminates in two jaws 94 which are bent outwardly to form a clamping element 95.

By squeezing the housing parts 10, 20 together in a direction of arrow Z, shown in FIG. 1A, the clamping element 95 can be operated via an integrated force-transmitting unit, generally designated by reference numeral 45. The force-transmitting unit 45 so interacts with the rod 98 of the functional unit 90 that both the rod 98 and the tube 96 are shifted relative to the stationary cutting element 95 in the direction of arrow X in opposition of the force of the compression spring 93, when the housing parts 10, 20 are squeezed together, i.e. in a direction substantially transversely to the support arm 30, to move over the clamping element 95 and thus to close the jaws 94, as shown in FIGS. 1E and 11B. By releasing the squeezing force, the housing parts 10, 20 move automatically apart again in direction of arrow Z' as a consequence of the spring force applied by the compression spring 93 on the rod 98 so that the tube 96 retracts in the direction of arrow X' and the jaws 94 are cleared again to assume the position shown in FIGS. 1D and 11A.

In the non-limiting example of FIGS. 1D, 11A, 1E, 11B, the clamp-type functional unit 90 is so configured that the distance of clamping point of the jaws 94 to the proximal end face of the sleeve 91 remains constant.

Although not shown in detail, it is, of course, also possible to so configure the functional unit 90 that the clamping element 95 can shift relative to the tube 96 in order to realize a clamping function of the jaws 94. In this case, the tube 96 is fixed to the sleeve 91 so that the clamping point shifts relative to the proximal end face of the sleeve 91.

Turning now to FIG. 1F, there is shown a variation of the functional unit 90 which is configured as a cutter-type operating member. The cutter-type operating member includes a guide sleeve 110 which is received in the coupling nut 97 and extends out through an opening of the coupling nut 97. Set ring 99 and interposed washer 100 are placed over the sleeve 110 and secured in place by threaded pin 101 so that the sleeve 110 and the coupling nut 97 form a unitary structure. The sleeve 110 has a bore 110.1 for movably receiving rod 98 which is formed with a blind bore 98.1 for accommodating a narrow portion 114.1 of an insert 114 which has a wider rod-distal portion 114.2 resting via a disk 112 against an inside wall surface of the sleeve 110 and supporting a shaft 109. The rod 98 issues from the rear of the sleeve 110 (FIG. 1B) for insertion into the head portion 35 and is formed with a slot 98.2 in which a pin 115, protruding from the insert 114, is guided. Inserted in the forward end of the sleeve 110 is a tube 106 which has a sleeve-distal end formed with a blade 107 of a cutting element 105. The shaft 109 is accommodated in and issues from the tube 106 and terminates in a blade 108. The shaft 109 and the insert 114 are interconnected by a set screw 111. Extending between the rod 98 and the wider portion of the insert 114 is compression spring 93 to bias the rod 98.

Figure 1G:
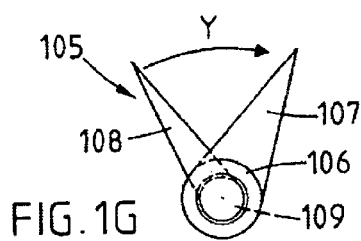
FIG. 1G is a schematic illustration, on an enlarged scale, of the two blades of the functional unit of FIG. 1F.

As the housing parts 10, 20 are squeezed in the direction of arrow Z, an axial displacement of the rod 98 in opposition of the spring force applied by the compression spring 93 causes a conjoint rotation of the insert 114 and the shaft 109 through interaction with the pin 115 about the longitudinal axis 109' (FIG. 1F), thereby moving the blade 108 toward the blade 107, as shown in FIG. 1G and indicated by arrow Y. In this configuration, the cutting area remains stationary in axial direction.

Referring now to FIG. 2A, there is shown a sectional view, on an enlarged scale, of the surgical instrument of FIG. 1A in the operative position after squeezing together the housing parts 10, 20. Each of the housing parts 10, 20 has an arcuate configuration (FIG. 2C) and is formed interiorly with a shoulder 11. The housing parts 10, 20 are of an identical construction, and hence only the housing part 10 will hereinafter be described, but it will be understood by persons skilled in the art that a description of the housing part 10 is equally applicable to the other housing part 20. At its rear end 200, the housing part 10 is formed integrally with a sheet-like member 14 which terminates in an end piece 15 of greater wall thickness, thereby defining the aforementioned pivot point to so bias the housing part 10 as to seek the inwardly deflected closed position. At its forward area, the housing part 10 is provided interiorly with a bearing, generally designated by reference numeral 25 and including a roller 27 which is rotatably supported by an axle 26. FIG. 2D shows a partial section of the support arm without the housing parts 10. 20 in a schematic representation where the stop members 23 are shown located in slot 33.

As shown in more detail in FIG. 2C, each housing part 10, 20 includes an inner pocket 12 for receiving the roller 27 which is secured in place on each of both sides by a sliding disk 28. As shown in FIG. 3A with reference to the housing part 10, the axle 26 of the roller 27 is secured in place, e.g. clamped, on opposite axial ends in an anchoring groove 13. FIG. 3B shows a cross section of the housing part 10, taken along the line III-III in FIG. 3A to depict the profile thereof.

When assembled, the housing parts 10, 20 are connected to one another and to the support arm 30, disposed therebetween, by pins 21 (cf. FIG. 2A) which extend through aligned bores 16 in the end pieces 15 and bores 34 in the support arm 30 (cf. FIGS. 5A, 5B), with the housing parts 10, 20 and the support arm 30 disposed in flat engagement in this area. As indicated by dash-dot line, the end cap 5 surrounds the area of the spring arms 14 and the end pieces 15. At its forward end, the flat elongate support arm 30 has a cylindrical sleeve 37 which terminates in the outwardly projecting head portion 35 and has an axial bore 38 for receiving a sliding bolt 41 of an adjusting member, generally designated by reference numeral 40, for transmitting an axial displacement into an actuation of the operating member of the functional unit 90. The sliding bolt 41 terminates in a slide piece 42 of substantially triangular configuration. The slide piece 42 is formed with converging sliding surfaces 43 which bear upon the rollers 27 of the housing parts 10, 20. A cutaway view of the adjusting member 40 is shown in FIG. 4A, with FIG. 4B illustrating a side view thereof. The bore 38 extends through the head portion 35 and terminates in a slot 32 of the support arm 30 for guiding the slide piece 42 during displacement between the operative position, shown in FIG. 2A and the idle position, shown in FIG. 2B in which the housing parts 10, 20 are moved apart in opposition to the elastic biasing force of the spring elements 14 on the housing parts 10, 20. A plan view of the support arm 30 is shown in FIG. 5A, with FIG. 5B illustrating a section view thereof, and FIG. 5C showing a section view, taken along the line V-V in FIG. 5B.

The sliding surfaces 43 of the adjusting member 40 have a flat configuration and converge to a pointed end. Of course, this configuration is shown by way of example only, and other configurations which generally follow the concepts outlined here are considered to be covered by this disclosure. For example, it is possible to provide the sliding surfaces 43 with a concave or convex configuration, as shown in FIGS. 4C and 4D, thereby implementing a progressive or degressive roll-off movement of the rollers 27 which are in engagement with the sliding surfaces 43.

As further shown in FIG. 2A, the support arm 30 is formed near the rear end with a slot 33 for receiving stop members 23 arranged in opposite disposition and suitably secured in bores 17 respectively formed in the housing parts 10, 20, for restricting a movement of the housing parts 10, 20 toward one another and securing the housing parts 10, 20 against a lateral deflection with respect to the support arm 30.

The surgical instrument according to the present invention operates as follows: When attaching the functional unit 90, such as the clamp-type operating member 95 or the cutter-type operating member 105, to the head portion 35 and securing the coupling nut 97, the rod 98 abuts against the confronting end of the sliding bolt 41 and pushes the adjusting member 40 between the rollers 27 to move the housing parts 10, 20 outwardly into the open position, shown in FIG. 2B, whereby the compression spring 93 exerts a sufficient spring force to overcome the biasing force applied by the spring arms 14 and thus a resistance of the housing parts 10, 20. In this position, the functional unit 90 is in idle position, i.e. the jaws 94 of the clamping element 95 are spread apart, when the clamp-type operating member 95 has been attached, or the blade 108 is moved away from the blade 107, when the cutter-type operating member 105 has been attached. As the housing parts 10, 20 are squeezed together, the adjusting member 40 is moved out to push the rod 98 in axial direction to thereby implement a closing of the jaws 94 or a movement of the blade 108, as described above. The adjusting member 40 is precisely guided between the rollers 29 in the slot 32 and the bore 38 and prevented hereby from rotating. This idle position is shown in FIG. 2B, and the operating member of the functional unit 90 is inactive. When the user squeezes the housing parts 10, 20 together, the rollers 29 move inwardly, thereby pushing the adjusting member 40 out and consequently moving the rod 98 to actuate the operating member of the functional unit 90, as shown in FIG. 2A.

Turning now to FIG. 6, there is shown a side elevation of another embodiment of a surgical instrument according to the present invention, generally designated by reference numeral 155. Parts corresponding with those in FIG. 1 are denoted by identical reference numerals and not explained again. In this embodiment, provision is made for a different type of force-transmitting unit which includes a pantographic linkage, generally designated by reference numeral 55, and adjusting member 40. In this embodiment, the adjusting member 40 has a forked or approximately inverted C-shaped bracket 57 (FIG. 10B), which is connected to the confronting end of shifting bolt 41, for hinged connection of the pantographic linkage 55 which includes a plurality of hingedly connected links and is guided in slot 32 of the support arm 30, as shown in FIGS. 7A and 7B, with FIG. 7A depicting the surgical instrument 155 in closed position as a result of the inherent elastic spring force, and FIG. 7B depicting the surgical instrument 155 in idle (open) position upon attachment of functional unit 90 such as clamp-type operating member 95 or cutter-type operating member 105. Although not shown in detail, of course the connection between the housing parts 10, 20 and the support arm 30 is realized in a same manner as described in conjunction with the embodiment of FIG. 1 via the spring arms 14 which bias the housing parts 10, 20 to seek the closed position, as shown in FIG. 7A.

In this embodiment, each of the housing parts 10, 20 has interiorly an axial recess 63, with the housing part 10 having a groove 62 which terminates in the axial recess 63 (FIGS. 7D and 7E), thereby forming a track for neighboring links of the pantographic linkage 55, and with the housing part 20 having two grooves 72 terminating in the axial recess 63 of the housing part 20 and separated by a web 76, as shown in FIGS. 7C, 8B and 8C.

FIG. 7C shows in more detail the arrangement of the pantographic linkage 55 in the housing 50. The pantographic linkage 55 has a link 54, arranged in the groove 62 of the housing part 10 and swingably mounted on a bolt 65, and two links 53, received in the grooves 72 of the housing part 20 and swingably mounted on a bolt 75. The housing part 10 is further formed with a bore 64 which extends transversely to the groove 62, as best shown in FIG. 7D for receiving the bolt 65 provided for support of the link 54. As shown in particular in FIG. 10A, a pin 58 extends through the bracket 57 for attachment of a link 52 and on each side thereof a link 51 (only one is visible here) of the pantographic linkage 55. The links 53 are hingedly connected to the other end of the link 52 on either side thereof and supported on a bolt 48. The link 54 of the pantographic linkage 55 is hingedly connected to the links 51, with the link 54 and the links 53 being supported by a bolt 47.

FIG. 8A shows a cutaway view of a detail of the housing part 20 and depicts the provision of a bore 74 which extends across the housing part 20 (cf. also FIG. 8B) for receiving the bolt 75.

The operation of the surgical instrument 155 is analog to the operation of the surgical instrument 150 and differs only in the translation of the force onto the adjusting member 40, when the housing parts 10, 20 are squeezed together, for actuating the operating member of the functional unit 90.

FIGS. 9A and 9B show cutaway views of a detail of the support arm 30. For realizing a sealed attachment of the functional unit 90, the head portion 35 is formed with a flange 84, and a sealing ring 83 is placed in an area between the flange 84 and the outer thread 36.

Surgical instruments involved here are very small in size so that a surgeon may be prone to confuse the type of instrument being intended for use. Therefore, the end cap 5 may be tinted with a color to differentiate the clamp-type surgical instrument from the cutter-type surgical instrument, i.e. the end cap 5 may have one color for the clamp-type surgical instrument, and another color for the cutter-type surgical instrument.

While the invention has been illustrated and described as embodied in a surgical instrument, it is not intended to be limited to the details shown since various modifications and structural changes may be made without departing in any way from the spirit of the present invention.

What is claimed as new and desired to be protected by Letters Patent is set forth in the appended claims:

What is claimed is:

1. A surgical instrument, comprising:

an elongate housing having two housing parts;

a support arm disposed between the housing parts and having opposite axial ends, with one of the axial ends connected to a rear end of the housing parts;

a functional unit configured for attachment to the other one of the axial ends of the support arm, wherein the functional unit includes a rod and an operating member acted upon by the rod, as the housing parts are squeezed together; and a force-transmitting unit having an adjusting member operatively connected to the rod, for translating a movement of the housing parts in a direction substantially transverse to the support arm, as the housing parts are squeezed together, into a linear axial movement of the adjusting member, to thereby actuate the operating member via the rod, wherein the adjustment member includes a wedge-shaped head having two sliding surfaces, and wherein the force-transmitting unit includes at least two rollers mounted in confronting disposition on opposite inner walls of the housing parts, said rollers interacting with the two sliding surface of the adjusting member.

2. The surgical instrument of claim 1, wherein the support arm has a head portion configured for threaded engagement of the functional unit, said head portion having an axial bore for guiding the adjusting member upon movement in axial direction.

3. The surgical instrument of claim 2, wherein the support arm has an axial slot connected to the axial bore for guiding the adjusting member during displacement in axial direction while being prevented therein from rotating.

4. The surgical instrument of claim 1, wherein the force-transmitting unit has a pantographic linkage including a plurality of links hinged to one another, said pantographic linkage being mounted at confronting inner walls of the housing parts and to the adjusting member.

5. The surgical instrument of claim 4, wherein the inner walls of the housing parts define tracks and wherein the support arm has a slot, said pantographic linkage guided and prevented from rotating in the tracks and having one end secured to the adjusting member and guided and prevented from rotating in the slot.

6. The surgical instrument of claim 4, wherein the adjusting member has a bracket of substantially inverted C-shaped configuration for hinged connection to the pantographic linkage by bolts.

7. The surgical instrument of claim 1, wherein the housing parts are swingably connected to the support arm at the one end via a spring-elastic mechanism by which a biasing force is applied upon the housing parts as to seek a position in which the housing parts when squeezed together are deflected inwards in an area confronting the functional unit.

8. The surgical instrument of claim 7, wherein the spring-elastic mechanism includes two plate-shaped spring arms and two end pieces formed integrally with the spring arms in one-to-one correspondence and configured for attachment to the support arm at the one end, one of the spring arms connected to one housing part and the other one of the spring arms connected to the other housing part.

9. The surgical instrument of claim 8, wherein the spring arms define a theoretical pivot point for allowing an outward deflection of the housing parts.

10. The surgical instrument of claim 1, and further comprising a stop mechanism located at the rear end of the housing parts and projecting into a slot of the support arm, for securing the housing parts against a lateral movement relative to the support arm.

11. The surgical instrument of claim 1, wherein the operating member is a clamping element securely fixed in place in the functional unit, said functional unit having a tube, which is operatively connected to the adjusting member and so configured that the tube is moved in axial direction relative to the stationary clamping element by the rod, when the housing parts are squeezed together.

12. The surgical instrument of claim 11, wherein the clamping element has two clamping jaws which are movable towards one another in opposition to an innate spring-elastic restoring force.

13. The surgical instrument of claim 1, wherein the operating member is a clamping element securely fixed in place in the functional unit, said functional unit having a tube and being so configured that a displacement of the adjusting member effects an inward movement of the clamping element into the tube, when the housing parts are squeezed together.

14. The surgical instrument of claim 13, wherein the clamping element has two clamping jaws which are movable towards one another in opposition to an innate spring-elastic restoring force.

15. The surgical instrument of claim 1, wherein the operating member is a cutting element having two blades, said functional unit including a slotted guide mechanism for converting an axial movement of the rod into a rotation movement of one blade into a direction towards the other blade, as the housing parts are squeezed together.

16. The surgical instrument of claim 1, and further comprising an end cap mounted to the rear end of the housing parts.

17. The surgical instrument of claim 16, wherein the end cap has a surface tinted with a color that is specific for the type of functional unit being attached.

18. The surgical instrument of claim 1, wherein the sliding surfaces are flat and converge to a common pointed end.

19. The surgical instrument of claim 1, wherein the sliding surfaces are concave and converge to a common pointed end.

20. The surgical instrument of claim 1, wherein the sliding surfaces are convex and converge to a common pointed end.

21. A surgical instrument, comprising:

an elongate housing having two housing parts;

a support arm disposed between the housing parts and having opposite axial ends, with one of the axial ends connected to a rear end of the housing parts;

a functional unit configured for attachment to the other one of the axial ends of the support arm wherein the functional unit includes a rod and an operating member acted upon by the rod, as the housing parts are squeezed together; and a force-transmitting unit having an adjusting member operatively connected to the rod, for translating a movement of the housing parts in a direction substantially transverse to the support arm, as the housing parts are squeezed together, into a linear axial movement of the adjusting member, to thereby actuate the operating member via the rod, wherein the force-transmitting unit includes at least two rollers mounted in confronting disposition on opposite inner walls of the housing parts, said rollers interacting with the adjusting member and wherein the adjusting member has a wedge-shaped head having two sliding surfaces bearing upon the rollers.

22. The surgical instrument of claims 21, wherein the sliding surfaces are flat and converge to a common pointed end.

23. The surgical instrument of claim 21, wherein the sliding surfaces are concave and converge to a common pointed end.

24. The surgical instrument of claim 21, wherein the sliding surfaces are convex and converge to a common pointed end.

* * * * *